United States Patent [19]

Dugger

[11] 4,372,366
[45] Feb. 8, 1983

[54] METHOD AND APPARATUS FOR NON-DESTRUCTIVE INSPECTION OF TIRES

[75] Inventor: Doyle L. Dugger, Muscatine, Iowa

[73] Assignee: Bandag Incorporated, Muscatine, Iowa

[21] Appl. No.: 233,967

[22] Filed: Feb. 12, 1981

Related U.S. Application Data

[62] Division of Ser. No. 31,961, Apr. 19, 1979, Pat. No. 4,285,235.

[51] Int. Cl.$^3$ ............................................. B29H 21/08
[52] U.S. Cl. ................................. 157/13; 51/DIG. 33
[58] Field of Search ............................ 73/146; 157/13; 51/DIG. 33, 105.91, 165.93

[56] References Cited

U.S. PATENT DOCUMENTS 3,965,959  6/1976  Weir ........................................ 157/13
4,241,300 12/1980 Hayes et al. ....................... 157/13 X
4,275,589  6/1981 Dugger et al. ......................... 73/146

Primary Examiner—James G. Smith
Attorney, Agent, or Firm—Cushman, Darby & Cushman

[57] ABSTRACT

A pulsed through-transmission ultrasonic non-destructive inspection of the internal structure in a tire wall is effected. The ultrasonic inspection is preferably carried out through the walls of a rotating inflated tire with the ultrasonic transducers being automatically moved toward the inner and outer tire wall surfaces to optimum relative distances of separation during an inspection cycle. The transducers disposed inside the inflated tire are preferably mounted for automatic retraction into a protected space during tire mounting and demounting operations. Such ultrasonic inspection techniques may be combined with conventional tire buffing methods and apparatus as practiced in tire retreading operations.

12 Claims, 5 Drawing Figures

METHOD AND APPARATUS FOR NON-DESTRUCTIVE INSPECTION OF TIRES

This is a division of application Ser. No. 31,961, filed Apr. 19, 1979, now U.S. Pat. No. 4,285,235.

This invention is generally directed to methods and apparatus for non-destructive inspection of rubber tires. Such inspection techniques may also be combined with conventional tire buffing operations in accordance with this invention.

The invention here claimed is directed to certain mechanical features of the preferred embodiment. The electrical features, per se are the sole invention of Morris D. Ho and are claimed in commonly assigned co-pending application Ser. No. 31,962 filed concurrently herewith. The combination of mechanical and electrical features is the joint invention of myself and Morris D. Ho and is claimed in commonly assigned copending application Ser. No. 31,963 filed concurrently herewith.

There has long been an urgent need for cost effective, efficient, non-destructive inspection (NDI) of rubber tire casings. There are obvious safety benefits to be had by such techniques if they can be efficiently and rapidly practiced. There are also potential economic benefits. For example, during tire retreading operations, a defective tire carcass can be discarded before wasting further expenditures of time and money if it can be accurately, efficiently and quickly detected.

In fact, the need for improved NDI methods and apparatus relating to the testing of tire casings is so great that the Army Materials and Mechanics Research Center has sponsored special symposia devoted entirely to this subject in 1973, 1974, 1976 and 1978. The proceedings of the first three of these symposia have now been published and are available from the National Technical Information Service. They each include a complete chapter on ultrasonic tire testing as well as other chapters devoted to different tire testing procedures (e.g. holographic, infrared and X-ray). There are also many prior art patents relating generally to the use of ultrasonic waves to non-destructively test pneumatic tire casings. For example:

U.S. Pat. No. 2,345,679—Linse (1944)
U.S. Pat. No. 2,378,237—Morris (1945)
U.S. Pat. No. 3,336,794—Wysoczanski et al (1967)
U.S. Pat. No. 3,604,249—Wilson (1971)
U.S. Pat. No. 3,815,407—Lavery (1974)
U.S. Pat. No. 3,882,717—McCauley (1975)
U.S. Pat. No. 4,059,989—Halsey (1977).

There are also several prior art patents relating to mechanical structures for chucking or otherwise physically handling pneumatic tire casings during various types of non-destructive testing or manufacturing processes. For example:

U.S. Pat. No. 2,695,520—Karsai (1954)
U.S. Pat. No. 3,550,443—Sherkin (1970)
U.S. Pat. No. 3,948,094—Honlinter (1976)
U.S. Pat. No. 4,023,407—Vanderzee (1977).

Although a wide variety of non-destructive ultrasonic tests have been performed on tires in the past as shown by these prior art patents, they have each suffered serious deficiencies and have failed to achieve widespread acceptance in commercial practice.

Prior tire chucking mechanisms in general have included axially movable tire mounting rims for quickly mounting and inflating a test tire. Prior NDI machines have located an ultrasonic transmitter inside a rotatable inflated, tire, albeit such have been only fixed or manually adjustable mounting arrangements. Other NDI machines have included articulated transmitter mounting arrangement in conjunction with a spread-open non-inflated test tire. However, there has not yet been a commercially viable mechanism arrangement for quickly positioning ultrasonic transducers about an inflated test tire wall while at the same time facilitating quick tire mounting/de-mounting procedures and also protecting the transducers from physical harm.

It has been discovered that these earlier attempts at ultrasonic non-destructive inspection of tire casings can be considerably improved and made more commercially viable.

The use of an inflated tire in the preferred embodiment has been discovered to assist in maintaining a true running tire surface and thus avoids signal variations that might otherwise be caused by wobbling or other relative axial motions of the tire walls during rotating. The inflated tire is also useful in helping to at least partially stress the tire walls, as they will be stressed during normal use, and to open up leakage passageways through the tire walls so that they may be detected by ultrasonic detection of air passing therethrough. Approximately only five psi is needed to maintain a stable inflated tire structure. However, it has been discovered that improved signal transmission and overall performance occurs if the tire is inflated within the range of approximately 15-18 psi.

Although it may not be required, it is preferred that the outer treadwall of the tire under inspection first be buffed to present a uniform surface thus minimizing spurious defect indications that might otherwise be caused by tread patterns and/or by uneven wear spots or patterns in the outer treadwall surface of the tire. In this connection, the tire buffing apparatus and method may be advantageously employed in combination with the ultrasonic non-destructive testing method and apparatus to present a unified, convenient and efficient overall operation. Since such a buffing operation is necessarily involved in tire retreading operations anyway, this combination is particularly attractive where the tire carcasses are being inspected in preparation for retreading.

The preferred exemplary embodiment of this invention includes special mechanical features for automatically moving the acoustic transducers into and out of operative position with respect to the inflated tire walls. During tire mounting and demounting operations, the acoustic transmitters are retracted inwardly both radially and axially with respect to at least one tire mounting ring or flange so as both to facilitate the tire mounting and demounting operations and to protect the acoustic transmitters from possible physical damage. During or after tire inflation, these acoustic transmitters are moved radially outwardly inside the inflated tire into an operative position with respect to the inside tire walls. At the same time, the array of acoustic receivers is moved radially inwardly towards the outer inflated tire walls to a desired operative position.

In the preferred exemplary embodiment, the relative axial movement of the acoustic transmitters with respect to a tire mounting flange or ring is achieved by spring loading the tire ring so that it axially moves away from the acoustic transmitters thereby uncovering them during the tire mounting operation and thus providing proper clearance for subsequent radially outward movement into the inflated tire carcass. Such spring loading also helps in properly seating the tire rims with the mounting flanges or rings during mounting and inflation operations.

These and other objects and advantages of this invention will be better appreciated by reading the following detailed description of the presently preferred exemplary embodiment in conjunction with the accompanying drawings, of which:

Figure 1:
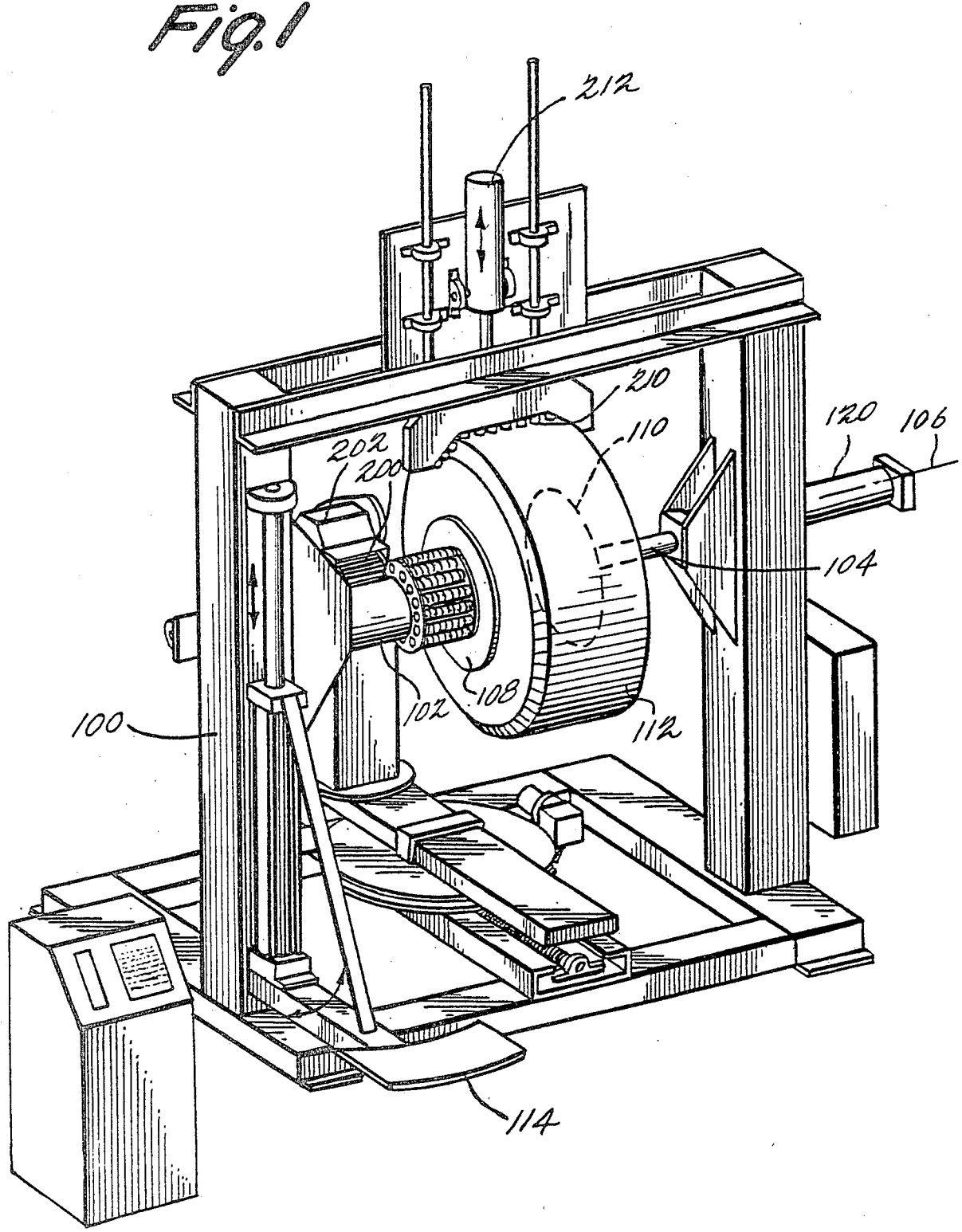
FIGS. 1 and 2 are perspective views of a combined NDI/buffer machine constructed in accordance with this invention.
Figure 2:
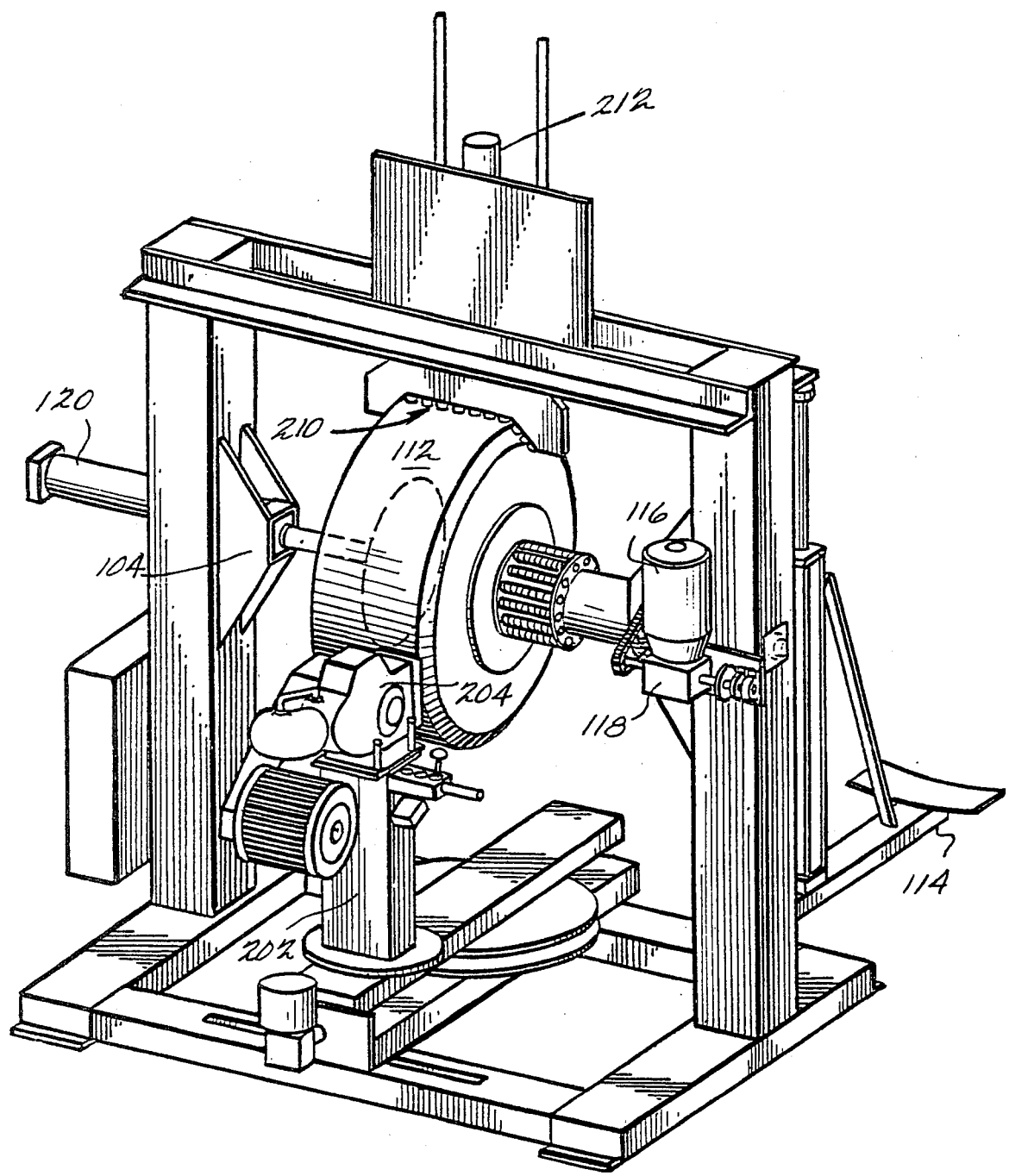

Referring to FIGS. 1 and 2, two perspective views of the presently preferred exemplary combined tire buffer and NDI machine are shown. As will be apparent, the NDI features of the machine may be provided, if desired, without including the tire buffing capability.

The major mechanical components of the machine are mounted to an open frame 100 having a fixed spindle 102 and an axially movable spindle 104 oppposingly aligned along horizontal axis 106. Conventional circular tire mounting rings or flanges 108 and 110 are attached to the outer rotatable ends of spindles 102 and 104 for mounting an inflated tire 112, therebetween. A conventional pneumatically operated tire lift mechanism 114 is conveniently provided so as to assist the human operator in lifting and swinging a tire into and out of place between rings 108 and 110 during tire mounting and demounting operations.

Ring 108, and hence tire 112, is driven by a two horsepower d.c. motor 116 through reducing gears 118. A tire surface speed of approximately 600 feet per minute is preferred for buffing operations while a much lower speed of approximately 40 feet per minute is preferred for NDI operations. Spindle 104, and hence ring 110, is axially extended and retracted by pneumatic cylinder 120. During tire mounting operations, ring 110 is retracted by cylinder 120 so as to permit the tire 112 to be lifted into place on ring 108 by lift 114. Thereafter, ring 110 is extended against the corresponding rim of tire 112 and the tire is inflated to a desired set point pressure by compressed air passed through the center of spindle 102.

A conventional rotating tire buffing rasp 200 is mounted on a vertical pedestal 202 situated on the backside of the machine as seen in FIG. 2. The rasp 200 is controlled via a conventional panel 204 to move laterally along a desired buffing path 206 and horizontally towards and away from the tire by conventional control mechanisms including a "joy stick" used to control lead screws and associated drive motors and the like. The buffer rasp 200 is rotated by a separate motor mounted on pedestal 202. The buffer mechanism, per se, is of a conventional type as marketed by Bandag, Inc., e.g. Buffer Model No. 23A.

An array of 16 ultrasonic acoustic receiving transducers 210 is disposed above and around the outer walls of tire 112. The receivers 210 preferably include a conically shaped collimator and/or focusing tube to help limit the field of view for each individual transducer to a relatively small and unique area across the tire wall. The receivers 210 may be conveniently potted either individually or in groups in a polyurethane foam or the like to help mechanically fix the receivers in their respective desired positions, to help protect the receivers and to help isolate the receivers from spurious ambient acoustic signals. The array of receivers 210 is radially adjusted into operative position by an air cylinder 212 having a coupled hydraulic control cylinder so as to define a radially extended operative position for the receivers 210.

Figure 3:
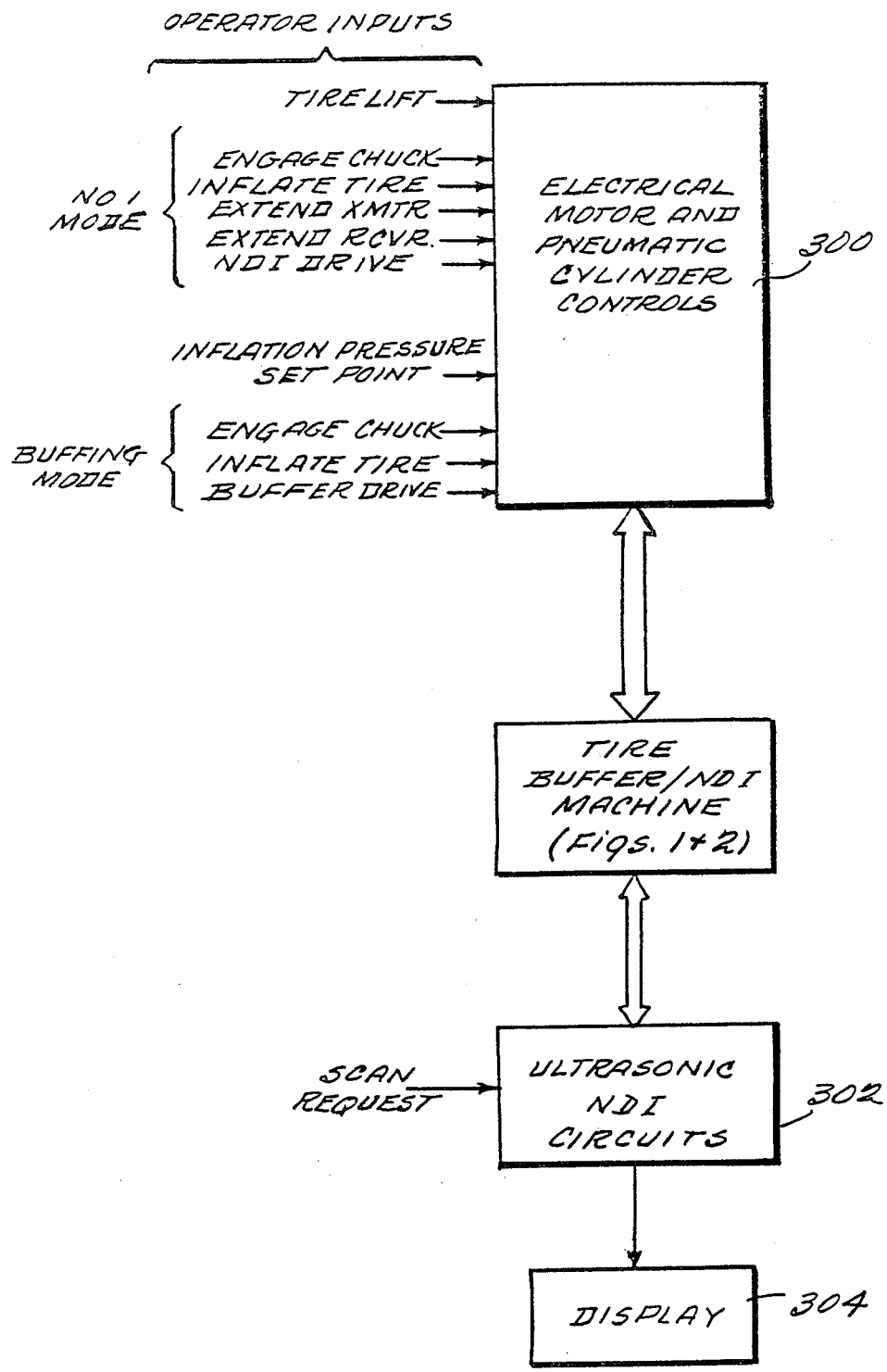
FIG. 3 is a block diagram of the invention shown in FIGS. 1 and 2.

A block diagram of the combined tire buffer/NDI machine and its associated electrical and pneumatic circuits is shown in FIG. 3. The electrical motor and pneumatic cylinder controls 300 are of entirely conventional design and thus not shown in detail. Operator inputs depicted at the left of FIG. 3 are made directly or indirectly by the operator via conventional electrical switches, relays, air valves and/or liquid control valves.

In operation, a tire is placed on lift 114 and raised into position between the rings 108 and 110. Preferably, a predetermined index position on the tire is aligned with a physical index position on flange 108. Thereafter, the chucking apparatus is engaged by causing flange 110 to move into the tire 112 so as to pinch the tire beads together in preparation for tire inflation. The tire is then inflated to a desired set point pressure. As will be explained in more detail below, the flange 108 is spring-loaded such that during chuck engagement and tire inflation, it is caused to move axially outwardly against the spring-loading (e.g. by approximately 2 inches). This facilitates the tire inflation process and simultaneously uncovers an ultrasonic transmitter located within the tire from a relatively protected position so that it may subsequently be extended into an operative position under the array of receivers 210. An interlock switch activated by air pressure and/or by the physical movement of flange 108 may be used to prevent any premature extension of the transmitter before it is uncovered from its protected position.

In the buffing mode, the transmitter need not be extended. The buffing rasp drive motors are conventionally activated and controlled (e.g. with a "joy stick" and conventional push button controls) to buff the tire tread surface as desired. Although it may not be required, it is presently preferred to have the tire buffed to a substantially uniform outer treadwall surface before NDI operations are performed. Such buffing is believed to avoid possible spurious indications of defects caused by normal tread patterns and/or by uneven wear about the tire surface.

When the operator selects the NDI mode of operation, an ultrasonic transmitter located inside the inflated tire 112 is extended into operative position and the array of receivers 210 is lowered into operative position by respectively associated pneumatic cylinders. The same 2-horsepower d.c. motor which drives the tire at approximately 600 surface feet per minute during buffing operations may be reduced in speed by conventional electrical circuits so as to drive the tire at approximately 40 surface feet per minute during the NDI mode. After the tire motion has reached a steady state, the operator may activate the scan request input switch to the ultrasonic NDI circuits 302. Thereafter the walls of tire 112 will be ultrasonically inspected during one or more complete tire revolutions to produce a display 304 which can be humanly interpreted directly or indirectly to reveal the condition of the tire (e.g. satisfactory for further buffing and retreading, doubtful or unsatisfactory). If questionable condition is indicated, the tire may be discarded or may be additionally buffed and retested.

Figure 4:
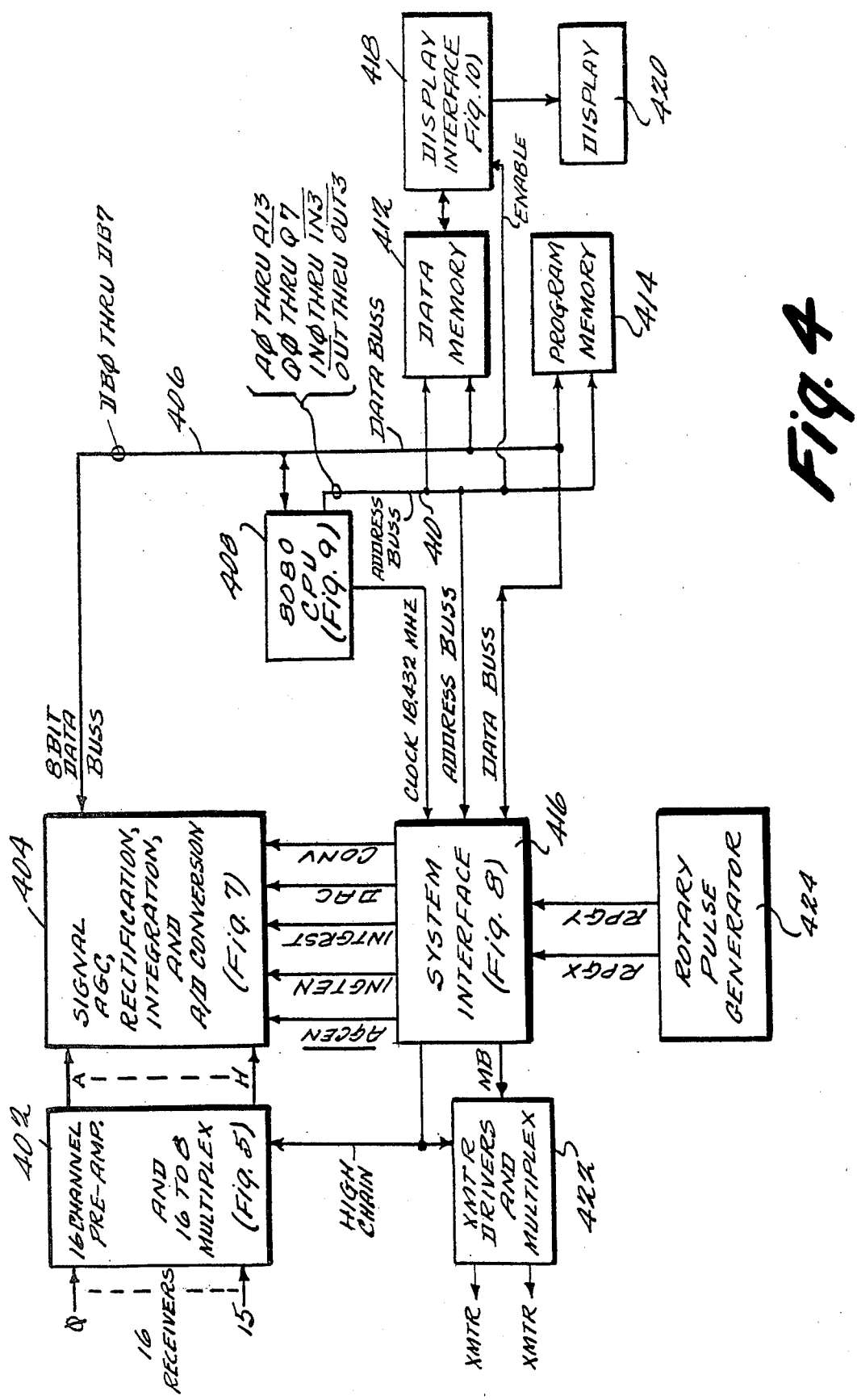
FIG. 4 is a block diagram of the ultrasonic NDI circuits which may be used in the NDI/buffer machine of FIGS. 1-3 or in a machine having only NDI capabilities.

The ultrasonic NDI circuits 302 are shown in greater detail at FIG. 4. The outputs from the 16 ultrasonic receivers 210 are amplified and multiplexed onto eight signal processing channels A-H by circuits 402. Each signal processing channel then provides AGC amplification, rectification, integration and analog-to-digital conversion with the signal processing circuitry 404. The resulting digitized outputs are presented to a conventional eight bit data bus 406 which is interconnected to a conventional micro-computer CPU (e.g. an 8080 type of eight bit computer) 408. The CPU 408 is also connected via a conventional address bus 410 and data bus 406 to a data memory 412, to a programmable read-only memory (PROM) 414 and to a system interface circuit 416. A display interface 418 is directly connected to the data memory banks 412 to provide a CRT type of oscilloscope display.

The system interface 416 provides the necessary gating and other control signals to the signal processing circuitry 404 and also provides HIGH CHAN multiplexing signals to the preamplifier circuits 402 as well as to the transmitter drivers and multiplexing circuitry 422 used to drive plural ultrasonic transmitters. The operation of the entire system is synchronized to the rotational movements of tire 112 through a rotary pulse generator 424 directly driven with the tire (e.g. geared to the reducer gears). The rotary pulse generator 424 provides 1,024 pulses per revolution at terminal RPGX and 1 pulse per revolution at terminals RPGY.

Ultrasonic acoustic transmitting crystals 500 and 502 are disposed inside inflated tire 112, which is chucked between rings 108 and 110, rotatably secured to spindles 102 and 104, respectively. The electrical leads feeding transmitters 500 and 502 are fed out through the fixed spindle 102 to the transmitter activation circuits. Inflation air is likewise fed in through the center of spindle 102 as are pneumatic lines and/or other control connections for extending and retracting the transmitters.

The exemplary ultrasonic transmitters 500 and 502 have a radiation field which substantially illuminates a sector of approximately 90°. Hence, they are mounted at 90° with respect to one another on block 504 which may, for example, be formed from polyvinyl chloride plastic materials. It has been found that acceptable operation will not result if the transmitters are too close to the inside tire surfaces or too far away from these surfaces. In the preferred exemplary embodiment, transmitting crystals 500 and 502 are approximately two inches from the inner tire wall surfaces although this optimum distance of separation may be varied by a considerably amount (e.g. plus or minus approximately one inch).

The arrayed receiving transducers 210 are located about an arc generally corresponding to the outside shape of the tire wall. Here again, it has been found that acceptable operation does not result if the receivers are too close or too far away from the outer tire walls. Preferably, the receivers are no closer than approximately 1 inch to the outer tire surface but are preferably within 5.5 to 8.5 inches of the opposingly situated transmitting crystal. The receiving transducers 210 preferably each employ a conically shaped collimator and/or focusing tube as shown in detail at FIG. 12. tubes are preferably machined from polyvinyl chloride plastic material and also help to match the impedance of the actual transducer crystal surface to the surrounding ambient air acoustic impedance.

A moderately high ultrasonic frequency is employed so as to help avoid interference from spurious ambient acoustic signals and to obtain increased resolution by using shorter wavelength acoustic signals while at the same time avoiding ultra-high frequency acoustic signals and the problems associated therewith. Frequencies above 40 kHz are desirable with 75 kHz being chosen as the presently preferred optimum frequency.

Figure 5:
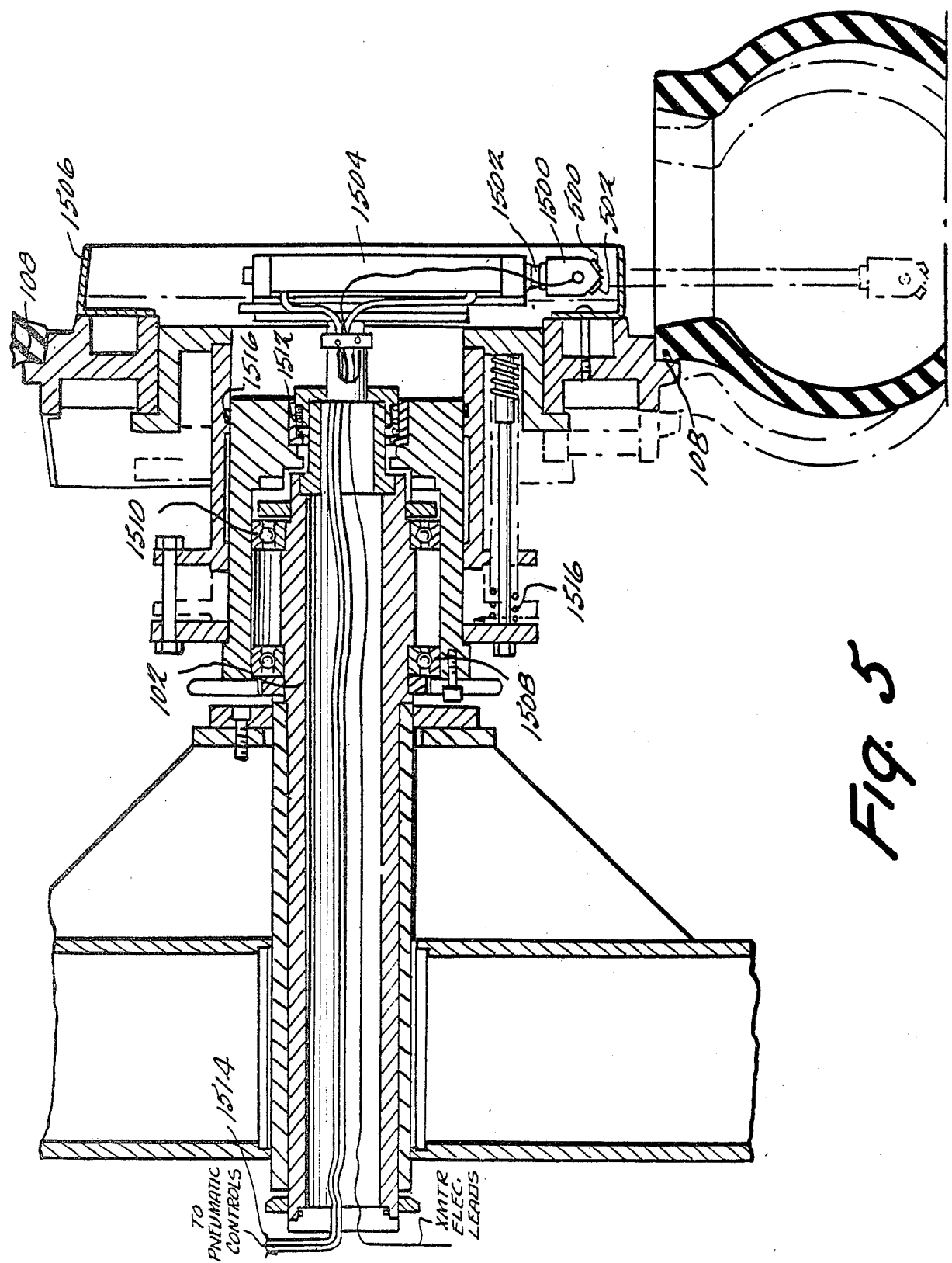
FIG. 5 is a detailed cut-away cross-sectional view of the fixed spindle and transmitter mounting arrangement used in the embodiment of FIGS. 1 and 2.

Greater detail of the fixed spindle 102 and of the associated transmitter mounting arrangement is shown in the cross-section of FIG. 5. The transmitting crystals 500 and 502 are directed at 90° with respect to one another from the face of a PVC mounting block 1500. The block 1500 is, in turn, attached to a retractable rod 1502 connected to the piston of a pneumatic cylinder 1504.

As shown in FIG. 5, the pneumatic cylinder 1504 has retracted the transmitting crystals 500 and 502 into a protected area defined by an annular plate 1506 attached to the tire mounting ring or flange 108. The tire mounting ring 108 is rotatably secured to the fixed spindle 102 through ball-bearing assemblies 1508 and 1510. This rotatable connection is maintained airtight by rotating seal assembly 1512. The center of the spindle 102 is hollow so as to permit passage of pneumatic control line 1514 and of the transmitter electrical leads therethrough.

The rotating ring 108 and its connected assembly is spring-loaded via spring 1517 to its axially extended position as shown in FIG. 15. However, the ring 108 may be moved axially to the position shown in dotted lines against the spring force. In the preferred exemplary embodiment, such motion begins to occur when the ring 108 has approximately 1500 lbs. of lateral force applied thereto. The sliding joint which permits such motion is also maintained air tight by "O" ring 1516. In the exemplary embodiment no more than approximately two inches of axial movement are permitted before the spring force is sufficient to resist further movement even when the tire is inflated to approximately 15-18 psi.

When the ring 108 is axially moved to the left as shown by dotted lines in FIG. 5 against the force of spring 1517, transmitters 500 and 502 are then exposed and the pneumatic cylinder 1504 can be activated to extend the transmitter into the position shown by dotted lines in FIG. 5 for an operative measurement cycle. Suitable interlocking switches activated by the internal pressure of the inflated tire and/or by the physical axial position of ring 108 can be employed to insure that pneumatic cylinder 1504 is not erroneously extended and damaged while the transmitters 500 and 502 are still enclosed and protected by the flange 1506.

While only a few exemplary embodiments and only a few variations thereof have been explained in detail, those in the art will appreciate that many other modifications and variations may be made without departing from the novel and advantageous features of this invention. Accordingly, all such modifications and variations are intended to be included within the scope of this invention as defined by the appended claims.

What is claimed is:

1. Apparatus for buffing and for nondestructively testing a buffed tire carcass, said apparatus comprising:
opposing circular rings for sealingly engaging the corresponding rims of said tire, tire inflation means for inflating said tire after engagement by said rings, buffing means for rotating said inflated tire and for buffing away the outer tread wall surfaces to provide a substantially uniform outside tread wall surface on the resulting tire carcass, ultrasonic testing means disposed both inside and outside said inflated tire for measuring the relative strengths of ultrasonic acoustic signals transmitted through different areas of said buffed tread wall as it is rotated thereby non-destructively testing the buffed tire carcass.

2. Apparatus as in claim 1 wherein said ultrasonic testing means comprises:

at least one ultrasonic acoustic transmitter, and adjustable transmitter mounting means mechanically mounted between said rings for retracting said transmitter radially toward the center of the circular rings while mounting and de-mounting the tire from between said rings and for extending said transmitter radially away from the center of the circular rings and toward the tire tread wall during testing.

3. Apparatus as in claim 1 wherein said adjustable transmitter mounting means is, when in its radially retracted position, also moved axially with respect to at least one of said rings so as to facilitate the tire mounting operation without damage to said transmitter.

4. Apparatus as in claim 1 further comprising:

a plurality of ultrasonic acoustic receivers relatively disposed in an array generally conforming to the outside cross-sectional shape of said tire, and adjustable receiver mounting means disposed for automatic retraction of said receivers radially away from said circular rings while mounting and de-mounting the tire from between the rings and for extending said receiver radially toward said circular rings during a measurement cycle.

5. Apparatus as in claim 1 wherein, during testing, said transmitter is disposed at approximately 2±1 inches from the inside tire wall surface and said receiver is disposed at approximately 4.5 to 8.5 inches from said transmitter.

6. Apparatus as in any one of claims 1-5 wherein said tire inflation means inflates said tire to a pressure of approximately 15 to 18 psi.

7. Method for buffing and for nondestructively testing a buffed tire carcass, said method comprising:

sealingly engaging the rims of said tire between opposing rings, inflating said tire after engagement by said rings, rotating said inflated tire and buffing away the outer tread wall surfaces to provide a substantially uniform outside tread wall surface on the resulting tire carcass, and measuring the relative strengths of ultrasonic acoustic signals transmitted through different areas of said buffed tread wall as it is rotated thereby non-destructively testing the buffed tire carcass.

8. Method as in claim 7 wherein said measuring step comprises:

retracting an ultrasonic transmitter radially toward the center of the circular rings while mounting and de-mounting the tire from between said rings and extending said transmitter radially away from the center of the circular rings and toward the tire tread wall during testing.

9. A method as in claim 7 wherein said transmitter, when in its radially retracted position, is also automatically moved axially with respect to at least one of said rings so as to facilitate the tire mounting operation without damage to said transmitter.

10. A method as in claim 7 further comprising:

retracting ultrasonic receivers radially away from said circular rings while mounting and de-mounting the tire from between the rings and extending said receivers radially toward said circular rings during a measurement cycle.

11. A method as in claim 7 wherein, during testing, an ultrasonic transmitter is disposed at approximately 2±1 inches from the inside tire wall surface and an ultrasonic receiver is disposed at approximately 4.5 to 8.5 inches from said transmitter.

12. A method as in any one of claims 7-11 wherein said tire is inflated to a pressure of approximately 15 to 18 psi.

* * * * *